(12) United States Patent
Chi

(10) Patent No.: US 9,615,761 B2
(45) Date of Patent: Apr. 11, 2017

(54) METHODS AND APPARATUS FOR MEASURING INDIVIDUAL ELECTRODE IMPEDANCES

(71) Applicant: COGNIONICS, INC., San Diego, CA (US)

(72) Inventor: Yu Mike Chi, San Diego, CA (US)

(73) Assignee: Cognionics, Inc., San Diego, CA (US)

( * ) Notice: Subject to any disclaimer, the term of this patent is extended or adjusted under 35 U.S.C. 154(b) by 0 days.

(21) Appl. No.: 14/782,978

(22) PCT Filed: Mar. 6, 2014

(86) PCT No.: PCT/US2014/021081
§ 371 (c)(1),
(2) Date: Oct. 7, 2015

(87) PCT Pub. No.: WO2014/138356
PCT Pub. Date: Sep. 12, 2014

(65) Prior Publication Data
US 2016/0113540 A1  Apr. 28, 2016

Related U.S. Application Data

(60) Provisional application No. 61/774,534, filed on Mar. 7, 2013.

(51) Int. Cl.
  A61B 5/04    (2006.01)
  A61B 5/0424  (2006.01)
  A61B 5/00    (2006.01)

(52) U.S. Cl.
  CPC .......... *A61B 5/0424* (2013.01); *A61B 5/6843* (2013.01)

(58) Field of Classification Search
  CPC ..................... A61B 5/0424; A61B 5/6843
  See application file for complete search history.

(56) References Cited

U.S. PATENT DOCUMENTS 5,704,351 A * 1/1998 Mortara ............... A61B 5/0006
                                                       128/904
6,546,270 B1 * 4/2003 Goldin ................... A61B 18/12
                                                       600/374

* cited by examiner

*Primary Examiner* — Rex R Holmes
(74) *Attorney, Agent, or Firm* — Edward W. Callan

(57) ABSTRACT

Electrode impedances on a body of a subject are measured by connecting a sense electrode, a reference electrode and a return electrode to the body, using the sense electrode to deliver a test current from a current source to the body of the subject, and measuring the potential difference between the sense electrode and the reference electrode. The impedance of the sense electrode on the body is measured in accordance with the measurement of the potential difference between the sense electrode and the reference electrode.

6 Claims, 1 Drawing Sheet

METHODS AND APPARATUS FOR MEASURING INDIVIDUAL ELECTRODE IMPEDANCES

DESCRIPTION

This invention relates to circuit designs for measuring electrode impedances in biopotential acquisition systems such as ECGs, EEGs or EMGs. In a practical biopotential system, it is often desirable to measure the impedance of the electrode connecting acquisition circuitry to the body of a subject. Electrode impedance values allow for the determination of both system failure (e.g., electrodes have fallen off) and signal quality (e.g., impedance too high resulting in extra noise). An impedance monitoring feature is especially critical in higher density applications (e.g., EEG systems, 12-lead ECG) to assist the user in the proper alignment and maintenance of electrodes to ensure optimum recordings.

Many impedance measurement techniques are based on the injection of a test current into the electrode. The impedance can be derived from Ohm's law by measuring the corresponding voltage developed across the electrode which is the impedance of the electrode multiplied by the test current (V=IR). In practical systems, the test signal is often an AC rather than DC current to avoid polarizing the electrode and to obtain a more accurate measurement by minimizing the effect of electrode offsets and drifts.

However, a fundamental difficulty exists with all current injection based impedance measurement techniques. Any current flowing into an electrode being measured must also circulate within the body of a subject and exit via a second electrode back into the electronics in order to complete a circuit. Likewise, any voltage measurement of potential differences must also involve two electrodes. In a typical biopotential electrode impedance measurement, the result is always the sum of two electrode impedances (Kim et al. Method and electronic medical device for simultaneously measuring and impedance and a biopotential signal, EP2294979 A1 and TI Application Note: Understanding Lead-Off Detection in ECG, SBAA196, May 2012). Although this may be sufficient for low-channel count applications such as ECG, higher density systems such as EEG critically require the knowledge of the impedance of an individual electrode to the body of a subject, isolated from other electrodes.

Separating out individual electrode contact impedances from the sums of electrode impedances is conventionally accomplished in a multi-channel array by taking the total impedance of various electrode pairs and algebraically solving for each individual electrode impedance. A typical example is described by Bibian et al. in U.S. Patent Application Publication: US 2011/0295096 A1. Although this scheme is effective for determining individual electrode impedances, the method requires that different pairs of electrodes be measured in sequence making it difficult to perform a measurement of the entire array at the same time. In many applications, it is desirable to measure all of the electrodes simultaneously with signal acquisition to measure contact quality throughout the experiment.

As previously explained, the fundamental issue with measuring individual electrode impedances is the need for determining the voltage, developed from a test current, across an individual electrode and not the sum of two electrodes. To determine the impedance of an individual electrode, the potential difference (voltage) of the electrode's two terminals must be known. The electrode's circuit side potential is directly accessible - it is the potential of the electrode's body side that is difficult to obtain. Ferree et al. in "Scalp Electrode Impedance, Infection Risk and EEG Data Quality," Clinical Neurophysiology v.112:3, 2001 describes a technique to force the body side potential to a known value by simulating a very low impedance voltage source by connecting all the electrodes in the array not under test to a stimulus source and measuring the response on the single electrode of interest. While this technique is effective for isolating single electrode impedances, it introduces significant circuit complexity in order to multiplex different electrodes between source and measurement mode. Furthermore, only a limited number of electrodes can be measured at any one time and simultaneous measurements of the array are not possible. Finally, since the technique attempts to simulate a low impedance source via the combination of many electrodes, this scheme necessarily only works on large-scale arrays (e.g., high density EEG) and not on lower channel count systems.

To achieve real-time, simultaneous measurement of individual electrode impedances, Danielssson et al. discloses a technique in U.S. Pat. No. 5,921,939 that utilizes a grounded return electrode to apply known stimuli to the body which appears as a common-mode signal to all the electrode channels. In normal usage, the common-mode test signal is cancelled out since biopotential measurements are by nature, differential. As the electrode contact impedance increases, the common-mode test stimuli are converted to a differential signal via the voltage division between the electrode impedance and each channel's amplifier input impedance. The effective impedance of each individual electrode can be determined by observing the amount of test stimulus that appears in each channel's output. This method is effective for determining electrode impedances at the individual level but has a key drawback. A priori knowledge of each channel's input impedance is necessary for accurate results. This often requires an explicit input shunt on each channel, which necessarily degrades the performance of the system, especially with dry, high-impedance electrodes.

In light of the limitations above, the invention allows for the measurement of an electrode's individual impedance by facilitating the measurement of the body side potential to isolate the voltage difference across individual electrodes. Rather than measuring the difference across the test electrode and the electrode for the current return path, a third 'reference' electrode which does not carry current is used. Because the reference electrode does not carry current into the body, the electrical potential of the reference electrode follows the body without the need for simulating a low-impedance source as with the scheme disclosed by Ferree et al. In a sense, the invention is inspired by the well-known 4 electrode, Kelvin sense technique, which is also used in biomedical applications to measure the impedance of underlying tissue, separate from the impedance of the measurement and stimulus electrodes. Recognizing that the impedance of body tissue is orders of magnitude smaller than the impedance of a surface electrode makes it possible to construct the current invention which involves three points (two for current stimulus, and a third reference) to measure the impedance of individual electrodes.

The invention provides circuit apparatus for measuring individual electrode impedances. A test current is injected into a sense electrode. A return electrode serves as a path for the test current to flow back into the measurement circuitry. A third electrode, without any test current flowing through it serves as a reference electrode. Because there is no current through the reference electrode, the potential of the reference electrode closely approximates the underlying potential of the body. Therefore, measuring the voltage between the sense electrode and the reference electrode recovers just the isolated impedance of the sense electrode irrespective of the return electrode's own contact impedance. The invention can be extended to an arbitrary number of channels by adding a test current source for each of the sense electrodes in the array and measuring the potential difference between the reference electrode and each of the sense electrodes. By modulating the test current at a frequency outside of normal signals, the measurements in the array can occur simultaneously and in the background with signal acquisition. For improved performance, a driven right leg amplifier can also serve as the return for the test current instead of a passive ground. The use of the active ground compensates for the test currents and keeps the potential of the body to a known value irrespective of the impedance of the return electrode or the magnitude of the test currents.

Figure 1:
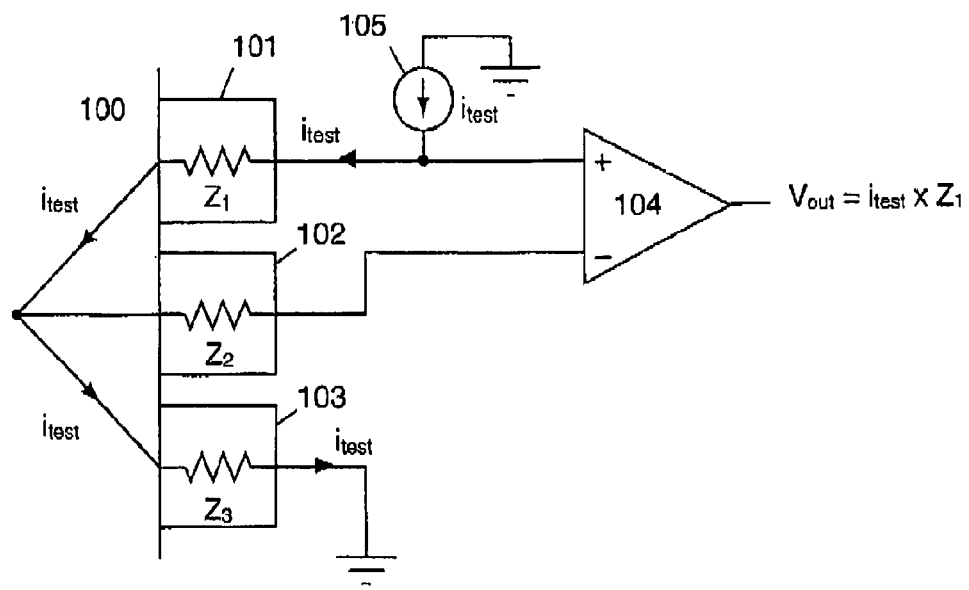
FIG. 1 is a schematic circuit diagram showing a first embodiment of the invention with a passive ground.

Referring to FIG. 1, a first embodiment of the invention is a one channel system for simplicity of illustration. The circuit apparatus includes three electrodes for connections to the body of a subject 100, to wit: a sense electrode 101, a reference electrode 102 and a return electrode 103; and a differential amplifier 104. Each electrode 101, 102, 103 has an associated impedance: Z1 for the sense electrode 101, Z2 for the reference electrode 102 and Z3 for the return electrode 103. There also exist internal impedances inside the body 100, but for most purposes they can be assumed to be negligible because the internal body tissues have orders of magnitude lower impedances than the surface electrodes Z1, Z2, Z3. Therefore, all electrodes can be considered as being internally connected by a low resistance wire inside the body of the subject 100.

To measure the contact impedance of the sense electrode 101, on the body of a subject 100, a current source 105 connected to the sense electrode 101 generates a known test current $i_{test}$. Normally this is an AC current source to avoid polarizing the electrodes and to avoid the offset errors associated with DC measurements. In the embodiment shown, the test current $i_{test}$ is set at an amplitude of 24 nA and at a frequency of 75 Hz to avoid harming the body of a subject. In practice $i_{test}$ is usually limited to less than a few microamperes for safety. The frequency is usually higher than 50 Hz to avoid contaminating the physiological measurement, but can be any frequency that can be acquired by the circuitry, including DC.

As illustrated by FIG. 1, $i_{test}$ flows into the body of a subject 100 through the sense electrode 101 and back out to via the return electrode 103 to complete the circuit. The flow of current $i_{test}$ generates associated potential differences across Z1 ($i_{test} \times Z1$) and Z3 ($i_{test} \times Z3$). With prior art methods, the total potential difference ($i_{test} \times (Z1+Z3)$) is recorded, which corresponds to the total impedances (Z1+Z3) of both the sense electrode 101 and the return electrode 103. However, it is the individual impedance Z1 of the sense electrode 101 that is usually desired. This can be extracted if the potential of the body of a subject 100 can be isolated from the potential across the return electrode 103 having impedance Z3.

The reference electrode 102 serves to measure the true potential of the body of a subject 100 by being connected to a differential amplifier 104 having a high input impedance. Since only a minimal current flows (e.g., input leakage on the order of picoamperes) through Z2 and into the inputs of the differential amplifier 104, the reference electrode 102 accurately tracks the potential of the body of a subject 100. Therefore, the impedance Z1 of the sense electrode 101 on the body of the subject 100 can be measured in accordance with the measurement of the potential difference between the sense electrode 101 and the reference electrode 102 by the differential amplifier 104, since such measured potential difference ($V_{out} = i_{test} \times Z1$) that is induced by the test current $i_{test}$ is purely due to the sense electrode's 101 impedance Z1.

For a multi-channel design (not shown), this scheme can be extended by replicating the test current source 105 and a differential amplifier 104 for every additional sense electrode 101 in the system. The other input of each differential amplifier 104 can all be connected to a common reference electrode 102 or to separate reference electrodes that also do not have a test current source and do not function as a current return. In a practical design, however, it is typically advantageous to utilize a common reference 102 electrode to minimize the number of parts and to simplify the system.

In most applications, the impedance of the return electrode 103 has minimal influence of the quality of the measurement but detecting whether or not it is placed correctly is useful in a practical device. The contribution of the reference electrode 102 is somewhat greater, especially if the reference electrode 102 is placed over an area of interest. It is therefore advantageous to be able to determine the impedance of both the reference electrode 102 and the return electrode 103 as well as the each of the sense electrodes 101.

Figure 2:
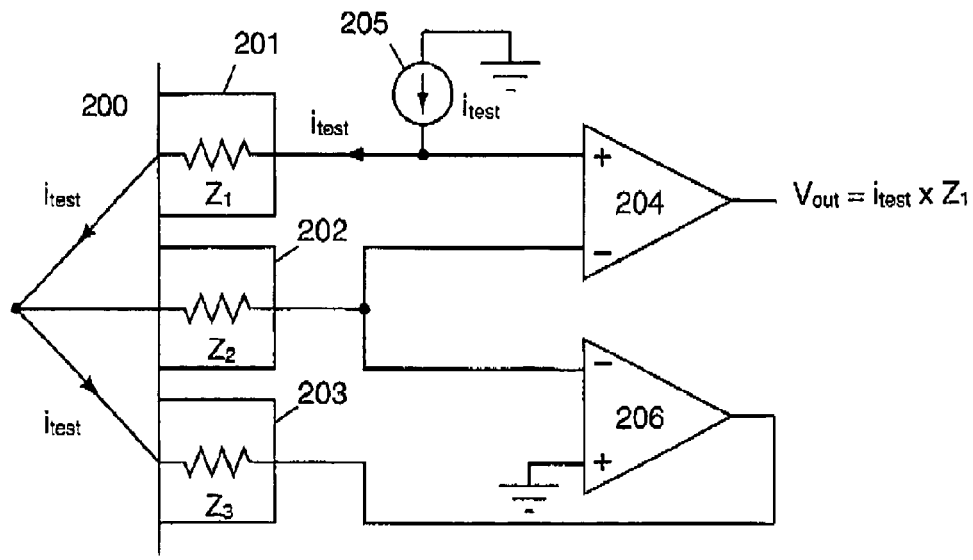
FIG. 2 is a schematic circuit diagram showing a second embodiment of the invention with an active ground.

FIG. 2 illustrates a second embodiment where the return electrode is replaced by a driven right leg amplifier circuit. As with the embodiment shown in FIG. 1, the system includes three electrodes for connections to the body of a subject 200, to wit: a sense electrode 201, a reference electrode 202 and a return electrode 203; and a differential amplifier 204. Each electrode 201, 202, 203 has an associated impedance: Z1 for the sense electrode 201, Z2 for the reference electrode 202 and Z3 for the return electrode 203. Likewise there exists a current source 205 associated with the sense electrode 201. Measuring both the impedance of the reference electrode 202 and the impedance of the return electrode 203 is made possible by the use of the driven right leg amplifier 206. As explained previously, the impedance Z3 of the return electrode 203 also develops a voltage due to the test current $i_{test}$ since it serves as the return path. The driven right leg amplifier 206 will compensate by applying a counteracting potential onto the return electrode 203 such that the potential on the reference electrode 202, and by extension the body of a subject 200, is equal to the circuit ground applied to the set point input of the driven right leg amplifier 206 (or some other reference potential supplied to the set point input of the driven right leg amplifier 206). Therefore, the impedance Z3 of the return electrode 203 can be determined by measuring the potential of the return electrode 203 (which is connected to the output of the driven right leg amplifier 206) with respect to the circuit ground (or some other set-point for the driven right leg amplifier 206). In a multi-channel system where multiple test currents are used for each channel, the measurement must account for the fact that the effective test current for the return electrode 203 is the sum of the test currents for each individual channel.

Measuring the impedance of the reference electrode 202 is slightly more complicated. At a basic level, the potential sensed by the reference electrode 202 should be very close to the reference point for the driven right leg amplifier 206. A basic 'lead-off' detection could be accomplished by determining that the potential at the reference electrode 202 is equal to the reference set point of the driven right leg amplifier 206, which is typically a circuit ground. A more sophisticated method to obtain the true impedance Z2 of the reference electrode could involve an additional test current source for the reference electrode 202. To measure the impedance of the reference electrode 202, this current source could be switched on while the current source 205 is shut off, in effect switching the roles of the sense electrode 201 and the reference electrode 202.

The above embodiment utilized a biopotential acquisition system to show the features of the invention. It is important to note that the measurement can also be broadly applied to any electronic circuit where measuring individual resistances/impedances are desired and is not limited to biomedical applications.

The invention can be used in a similar manner to other biopotential amplifier designs. The impedance measurement circuit can occur in the background with normal signal acquisition if the test current is at a frequency higher than the ECG/EMG/EEG bandwidth. The output of the biopotential amplifier will contain both the biopotential signal and the impedance measurement data. Impedance measurement data can be filtered out by a bandpass filter centered at the frequency of the current source and processed to recover the contact quality for each channel. An alert or display could be then used to show the impedance data and advise the user on the placement and adjustment of individual electrodes.

The invention claimed is:

1. Circuit apparatus for determining electrode impedances on a body of a subject, comprising,
   a sense electrode for delivering a test current from a current source to said body of said subject;
   a return electrode for connection to said body for providing a return path for said test current;
   a reference electrode isolated from any current source for connection to said body for measuring a potential of said body; and
   a differential amplifier for providing a measurement of a potential difference between the sense electrode and the reference electrode;
   wherein the impedance of the sense electrode on said body can be determined in accordance with said measurement of the potential difference between the sense electrode and the reference electrode.

2. The circuit apparatus of claim 1 comprising a plurality of said sense electrodes for connection to said body for delivering a plurality of test currents from a plurality of current sources.

3. The circuit apparatus of claim 1 further comprising:
   a driven right leg amplifier;
   wherein the reference electrode and the return electrode are connected in a feedback loop through the driven right leg amplifier, with the return electrode being connected to the output of the driven right leg amplifier, for biasing said body to a known potential for minimizing the effect of said test current on the potential of said body.

4. The circuit apparatus of claim 3,
   wherein the impedance of the return electrode can be determined by measuring the potential of the return electrode with respect to a set-point reference potential for the driven right leg amplifier.

5. The circuit apparatus of claim 1 wherein the reference electrode is connected to a current source for measuring the impedance of said reference electrode.

6. A method of determining electrode impedances on a body of a subject, to which a sense electrode and a return electrode have been connected, comprising the steps of:
   (a) using the sense electrode to deliver a test current from the current source to the body of the subject;
   (b) connecting to the body a reference electrode that is isolated from any current source;
   (c) using the return electrode to provide a return path for said test current;
   (d) using the reference electrode to measure a potential of said body; and
   (e) using a differential amplifier to provide a measurement of a potential difference between the sense electrode and the reference electrode;
   wherein the impedance of the sense electrode on said body is determined in accordance with said measurement of the potential difference between the sense electrode and the reference electrode.

* * * * *